United States Patent
Liu et al.

(10) Patent No.: US 7,375,245 B2
(45) Date of Patent: May 20, 2008

(54) N-(4-OXO-BUTANOIC ACID)-L-AMINO ACID-ESTER DERIVATIVES AND METHODS OF PREPARATION THEREOF

(75) Inventors: Yu-Liang Liu, Taipei (TW); Rung-Tian Suen, Taipei (TW); Ying-Chi Chiu, Taipei (TW)

(73) Assignee: Everlight USA, Inc., Pineville, NC (US)

( * ) Notice: Subject to any disclaimer, the term of this patent is extended or adjusted under 35 U.S.C. 154(b) by 0 days.

(21) Appl. No.: 10/885,092

(22) Filed: Jul. 7, 2004

(65) Prior Publication Data

US 2006/0009652 A1    Jan. 12, 2006

(51) Int. Cl.
*C07C 229/00* (2006.01)
*C07C 69/76* (2006.01)

(52) U.S. Cl. .............................. 560/39; 560/8; 560/19; 560/37; 560/38

(58) Field of Classification Search ............... 560/39, 560/8, 19, 37, 38
See application file for complete search history.

(56) References Cited

U.S. PATENT DOCUMENTS 4,925,969 A * 5/1990 Takahashi et al. ............ 560/41

* cited by examiner

*Primary Examiner*—Thurman K. Page
*Assistant Examiner*—Yevgeny Valenrod
(74) *Attorney, Agent, or Firm*—Bacon & Thomas PLLC

(57) ABSTRACT

The present invention provides a compound of the following formula (I):

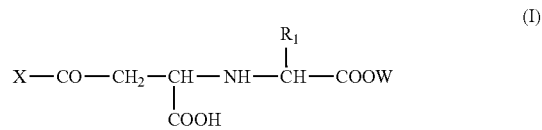

wherein $R_1$ is methyl or 4-aminobutyl, which may be acylated; X is phenyl or substituted phenyl; W is an esterified group removable by hydrogenolysis. Also disclosed is the preparation method and the application of formula (I) compound.

10 Claims, No Drawings

N-(4-OXO-BUTANOIC ACID)-L-AMINO ACID-ESTER DERIVATIVES AND METHODS OF PREPARATION THEREOF

BACKGROUND OF THE INVENTION

1. Field of the Invention

The present invention relates to N-(4-oxo-butanoic acid)-L-amino acid-ester derivatives, in particular to the preparation method and application of N-(4-oxo-butanoic acid)-L-amino acid-ester derivatives.

2. Description of the Related Prior Art

Recent years, with increase in average life expectancy of population, an advanced aged society had developed. Hypertension is one of the most common vasocular diseases within this group of people. As a consequence of this trend, medicines for reducing blood pressure had become even more demanding than before. Among all the drugs, ACE (Angiotensin Converting Enzyme) inhibitor is one of the drugs used for treating hypertension and heart failure. Unlike other drugs used for hypertension treatment, ACE inhibitor will not result in common side effects, they do not have central nervous system side effect. Moreover, ACE does not cause harmful interference with metabolism where diuretic does, it is also suitable for the population who suffers from asthma or diabetes, and therefore it is highly appreciate by the patients. The related kinds of reducing blood pressure medicines that had already been disclosed in U.S. patents are U.S. Pat. No. 4,542,234, Pat. No. 4,465,443, Pat. No. 4,480,874, Pat. No. 4,879,403, Pat. No. 4,925,969, Pat. No. 5,756,812 and Pat. No. 6,118,010.

SUMMARY OF THE INVENTION

The present invention provides the compound of N-(4-oxo-butanoic acid)-L-amino acid-ester derivatives. The present invention also provides the application and the preparation method for the above derivatives.

The compound of N-(4-oxo-butanoic acid)-L-amino acid-ester derivatives is a key intermediate for synthesizing the ACE inhibitors.

The compound of the formula (I) of the present invention is shown as below:

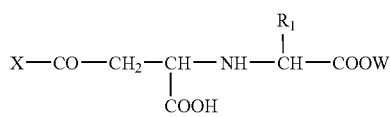
(I)

wherein $R_1$ is methyl or 4-aminobutyl, which may be acylated; X is phenyl or substituted phenyl; W is an esterified group removable by hydrogenolysis.

The compound of the formula (I) can be prepared by reacting (such as proceeding a Michael addition reaction) the following α-amino acid ester

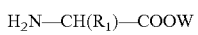

wherein $R_1$ and W are defined as the above formula (I) compound, with the following keto-acrylic acid

wherein X is defined as the above formula (I) compound.

The formula (I) compound of the present invention can be reacted with an esterification reagent by proceeding an esterification reaction. The reaction product is isolated by a fractional crystallization method. The above isolated product can then be used to manufacture antihypertensive drugs.

DETAILED DESCRIPTION OF THE PREFERRED EMBODIMENTS

The present invention provides a compound of the following formula (I):

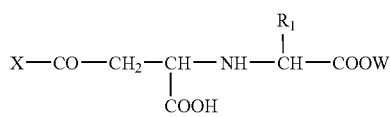
(I)

wherein $R_1$ is methyl or 4-aminobutyl, which may be acylated; X is phenyl or substituted phenyl; W is an esterified group removable by hydrogenolysis.

The 4-aminobutyl, which may be acylated of $R_1$ in the above formula (I) compound can be obtained by protecting the amino group of the α-amino acid ester. One example of the 4-aminobutyl, which may be acylated is shown below.

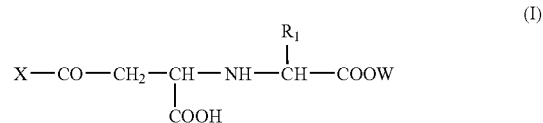

When the X of the compound of the formula (I) is a substituted phenyl, said substituted phenyl is preferred selected from the group consisting of

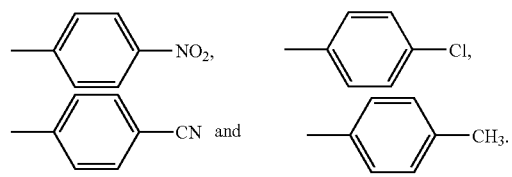

When the W of the formula (I) compound is an esterified group removable by hydrogenolysis, it means that the byproducts produced by the hydrogenation reaction could not affect the reaction. Examples of the protected group are: benzyl (the resulting byproduct is toluene) or isobutyl (the resulting byproduct is isobutane).

The formula (I) compound of the present invention is preferably the following formula (I-1).

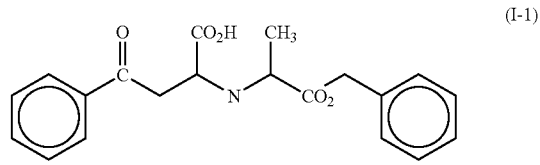
(I-1)

The formula (I) compound of the present invention can be prepared by reacting the following α-amino acid ester

Wherein $R_1$ and W are defined the same as above formula (I) compound, with the following keto-acrylic acid

X—CO—CH═CH—COOH

Wherein X is defined the same as above formula (I) compound, to proceed a Michael addition reaction.

The preparation method of the formula (I) compound of the present invention can further be described as the following scheme:

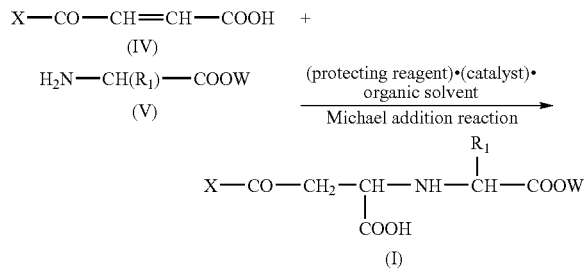

wherein, $R_1$, X and W are described the same as above.

As shown by the above reaction scheme, the formula (IV) compound is reacted with the formula (V) compound in the presence of organic solvent, with or without protecting reagent, and with or without catalyst to form the formula (I) compound.

The above organic solvent can be selected from the group consisting of high-polar organic solvent, medium-polar organic solvent, and chlorinated solvent. Examples of the above organic solvent are toluene, methylene chloride, dichloroethane, ethyl acetate, or N,N-Dimethyl formamide. It is preferred that said organic solvent are toluene, ethyl acetate, or N,N-Dimethyl formamide, and more preferably are toluene, or ethyl acetate.

In the above reaction, the effect of adding the protecting reagent is to increase the stereo selectivity (degree of freedom). Examples of the protecting reagents are: trimethylsilyl, chlorine trimethylsilyl, or chlorine triethylsilyl. It is preferred that said protecting reagents are trimethylsilyl, or chlorine trimethylsilyl, and more preferably is trimethylsilyl.

In the above reaction, the effect of adding the catalyst is to increase the reaction rate of Michael addition reaction. Examples of the catalysts are triethyl amine, dimethyl amino pyridine, or pyridine. It is preferred that said catalysts are triethyl amine or dimethyl amino pyridine.

There are no particular restrictions on the limit of reaction temperature. General speaking, the range of the reaction temperature is between 0° C. to 60° C. The reaction temperature depends on what kind of organic solvents used in the reaction. For example, in a reaction condition of high temperature, toluene is the ideal organic solvent. Contrarily, in a reaction condition of low temperature, ethyl acetate is suitable. The reaction time is also not strictly limited, it depends that the reaction is completed or not. It is preferred that said reaction time is 6 hours to 8 hours.

The formula (I) compound of the present invention can be further proceed with esterification:

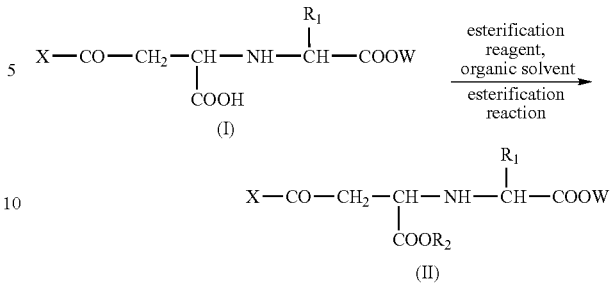

wherein $R_2$ is $C_1$-$C_6$alkyl; $R_1$, X and W are defined the same as above.

Examples of esterification reagents used in the above reaction are dimethyl sulfate, ethyl-sulfate, methyl bromide, or ethyl bromide. It is preferred that said esterification reagents are methyl sulfate, ethyl sulfate, or ethyl bromide and more preferably is methyl sulfate, or ethyl sulfate.

The above organic solvent can be selected from the group consisting of high-polar organic solvent, medium-polar organic solvent, and chlorinated solvent. Examples of the above organic solvent are toluene, methylene chloride, dichloroethane, ethyl acetate, or N,N-Dimethyl formamide. It is preferred that said organic solvent are toluene, ethyl acetate, or N,N-Dimethyl formamide, and more preferably are toluene, or ethyl acetate.

There are no particular restrictions on the limit of reaction temperature. General speaking, the range of the reaction temperature is between 0° C. to 60° C. The reaction temperature is dependent on what kind of organic solvents and esterification reagents used in the reaction. The reaction time is also not strictly limited, it depends that the reaction is completed or not. It is preferred that said reaction time is 8 hours to 10 hours.

The formula (II) compound formed by the above esterification reaction can be isolated by a fractional crystallization method. In the crystallization method, the crude product of the formula (II) compound is crystallized in the presence of alcohol solvent and the temperature between 0° C. to 50° C. Alcohol solvents such as methyl alcohol, ethyl alcohol, or isopropyl alcohol are used for the above crystallization, wherein methyl alcohol, or isopropyl alcohol is preferably.

The formula (II) compound of N-(1-alkoxycarbonyl-3-oxo-3-phenylpropyl)-L-amino acid-benzyl ester formed from the above esterification reaction can further be proceeded to a hydrogenation reaction as shown below:

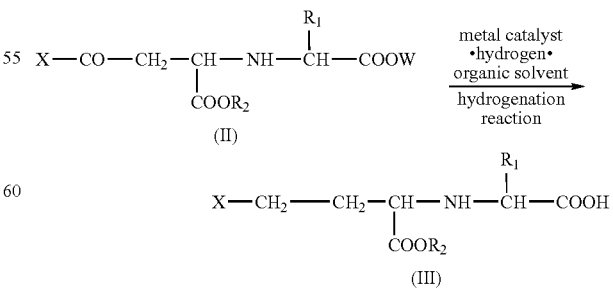

Examples of metal catalysts used in the above reaction scheme are raney nickel, rhodium, ruthenium, iridium, platinum, palladium, wherein Platinum or palladium is preferably, and palladium is the most preferred.

The organic solvent used in the hydrogenation reaction is an alcohol solvent. Examples of the alcohol solvents are methyl alcohol, ethyl alcohol, and isopropyl alcohol. It is preferred that said alcohol solvent are ethyl alcohol or isopropyl alcohol, and more preferably is isopropyl alcohol.

The range of temperature for the hydrogenation reaction of the present invention can be from 0° C. to 30° C., it depends on what kind of solvents used in the reaction. The reaction time is also not strictly limited, it is preferred that said reaction time is 5 hours to 10 hours.

After the above hydrogenation reaction is completed, the crude product is obtained. The crude product includes the formula (III) compound and other byproduct and it is need to precede a purifying process to remove the byproduct. The byproducts include all the impurities created during the reaction, for example, N-(1-carboxy-3-phenylpropyl)-L-amino acid, or N-(1-alkoxycarbonyl-3-cycloalkylpropyl)-L-amino acid.

The purifying method of the present invention includes putting the crude product of the formula (III) compound into the organic solvent/water, or acid/water solution to form a mixture solution. The mixture solution is heated to let the solid dissolve, and then the mixture solution is cooled to let the formula (III) compound be crystallized out.

The organic solvents used in the above purifying method must be miscible with water, for example ketone. It is preferred that said ketone is acetone. In the above acid/water solution, the acids can be acetic acid, hydrochloric acid, sulfuric acid and so on. Wherein acetic acid, and hydrochloric acid are preferably, and acetic acid is more preferably. Regarding to the volume ratio of the solution used for the purifying method, it is preferred that the volume ratio of organic solvent to water (or acid to water) is within 1 to 20.

The heating temperature for the purifying method of the present invention is above 55° C., and it is preferred that at a temperature of 60-70° C. After the solids are dissolved completely, the solution is filtered. The filtrate is then cooled to the room temperature, and it is preferred that at a temperature of 20° C. to 30° C. After the filtrate is cooled, the formula (III) compound is crystallized out. The purity percentage of the crystalline formula (III) compound is greater than 99%, and the other impurities are all lower than 0.1%.

The formula (I) compound of N-(4-oxo-butanoic acid)-L-amino acid-ester derivatives of the present invention is obtained by using (E)-acrylic acid and α-amino acid-ester to undergo a Michael addition reaction. The formula (I) compound can be formed the formula (II) compound by proceeding an esterification reaction in a weak basic and room temperature. The formula (II) compound is then hydrogenated and purified to form formula (III) compound. In comparison with conventional method, the preparation method of the present invention can be shorten the reaction time and decrease the danger during the reaction.

More detailed examples are used to illustrate the present invention, and these examples are used to explain the present invention. The examples below, which are given simply by way of illustration, must not be taken to limit the scope of the invention. Any skilled personnel in the field can simply modify or amend the invention and it is all included in the following area. Unless specifically specify, the examples are in weight percent, and temperature unit is in degree Celsius ° C.

EXAMPLE 1

Preparation of Compound Formula (I-1)

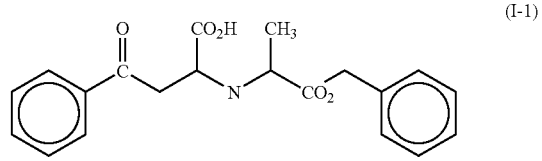

17.6 g of (E)-3-benzoylacrylic acid, 20.3 g of N,N'-Bis(trimethylsilyl) urea, and 80 g of ethyl acetate were mixed in a 250 ml reaction flask equipped with a mechanical stirrer. The solution was then stirred uniformly for an hour at 40-50° C. The reacted solution was filtered, and allow the filtrate to cool until it reaches 0-5° C., then 18.8 g of L-alanyl-benzyloxy ester was added. The solution was continuously stirred for another 6 hours in order for reaction to take place and afterwards 6.0 g of isopropyl alcohol and 50 ml of cyclohexane were added. At this point precipitates were formed in the reaction flask. The precipitates were filtered and the product of light yellow power was obtained and weights about 25.4 g.

$^1$H NMR(DMSO-d6):

δ1.15-1.22(m,3H), δ3.30-3.38(m,2H), δ3.53-3.59(q,1H), δ3.68-3.72(t,1H), δ5.08-5.19(d,2H), δ7.29-7.38(m, 5H), δ7.49-7.54(t,2H), δ7.61-7.68(t,1H), δ7.91-7.96(d,2H)

EXAMPLE 2

Preparation of Compound Formula (II-1)

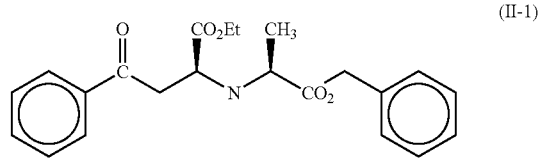

8.9 g of formula (I-1), 40 ml of dimethyl formamide, 2.5 g of triethylamine, and 2.38 g of diethyl sulfate were added to a 100 ml reaction flask, the solution in the beaker were then stirred at 0-5° C. for 8 hours. After the solution were heated to 20-25° C. meanwhile 30 ml of water were added into the reaction flask and uniformly stirred for half an hour, then the solution were at a standstill for phase layers were divided. The organic layer of the solution was taken and 5 g of sodium sulfate were added. The organic solution was stirred for half an hour then the solution was filtered. After the filtrate was condensed and a light yellow oily substance was obtained. 20 ml of isopropyl alcohol was added to the oily substance, stirred for one hour under 20-25° C., then the temperature is dropped to 0-5° C. and again stirred for another 2 hours. The reacted substance was filtered, and a white solid of 1.56 g were obtained.

$^1$H NMR (DMSO-d6):

δ 1.20-1.24(d,2H), δ 1.34-1.37(d,2H), δ 3.40-3.44(m,2H), δ 3.60-3.70(q,1H), δ 3.80-3.82(t,1H), δ 4.13-4.19(q,2H), δ 5.12-5.14(d,2H), δ 7.30-7.34(m,5H), δ 7.41-7.46(t,2H), δ 7.52-7.55(t,1H), δ 7.89-7.92(d,2H)

EXAMPLE 3

Preparation of Compound Formula (III-1)

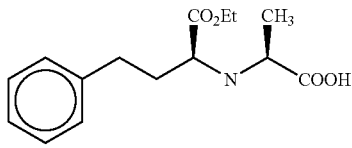

Under 20-25° C. pressurize hydrogen environment, 26.6 g of formula (II-1), 2.6 g of pd/C, 93 g of isopropyl alcohol and 10.7 g of methanesulfonic acid were reacted for 10 hours in a 250 ml hydrogenation reactor. Reacted solution was washed and filtered by 13.0 g of celite for the removal of pd/C. The pH of the filtrate is then adjusted to 2.0-2.7 by 20% sodium hydroxide solution. Concentrate the filtrate to remove isopropyl alcohol, then 10 g of water and 2.5 g of acetone were added to the filtrate. Follow the above procedure, 20% of sodium hydroxide solution was then used to adjust the pH to 5.5-6.0, and white solids were formed as the product. Solids were filtered and dried in an oven for the moistures to evaporate. White solids of 13.6 g were obtained.

$^1$H NMR (MeOH-d4):

δ 1.16-1.40 (t,3H), δ 1.40-1.68(d,3H), δ 2.06-2.32(q,2H), δ 2.56-2.90(m,2H), δ 3.44-3.64(q,1H), δ 3.88-4.10(t,1H), δ 4.10-4.40(q,2H), δ 7.08-7.44(m,5H)

EXAMPLE 4

Purification of Compound Formula (III-1)

9.29 g compound of formula (III-1), 30 ml of acetone, and 20 ml of water were mixed in a 250 ml three-neck bottle. The three-neck bottle was heated in a water bath to 60° C., and the solution contained in three-neck bottle was stirred until all solids were dissolved. The above solution was then filtered and collected at 60° C. The temperature of the obtained filtrate were then decreased to 53~55° C. 0.1 g of formula (III-1) was added to the resultant filtrate as crystal seeds, the temperature was maintained constantly for half an hour, then the temperature was dropped to 0~5° C. The product was filtered and dried to yield 7.4 g of white solids. The melting point of the product is 151~152° C. with purity greater than 99%, impurities N-(1(S)-carboxy-3-phenylpropyl)-L-alanine contained less than 0.1%, and N-(1(S)-1-ethoxycarbonyl-3-cyclohexylpropyl)-L-alanine were also less than 0.1%.

Differ from the traditional methods, the preparation method of the present invention starts with Michael addition reaction first then proceeds with an esterification reaction. It avoids fierce reaction condition, moreover it only requires weak base and room temperature for esterification reaction to take place, at the same time it reduce the reaction time. Comparable to traditional methods, the present invention greatly increases manufacture efficiency, reduces manufacture hazards, and more.

From the foregoing description, one skilled in the art can easily ascertain the essential characteristics of this invention, and without departing from the scope thereof, one can make various changes and modifications of the invention to adapt it to various usages and conditions. Thus, other embodiments are also within the claims.

What is claimed is:

1. A compound of the formula (I):

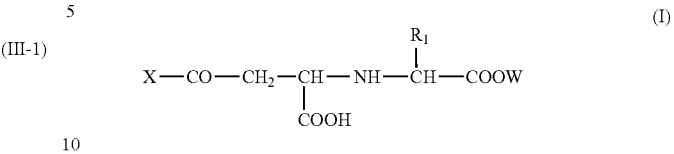

wherein:

$R_1$ is methyl or 4-aminobutyl, which may be acylated;

X is phenyl,

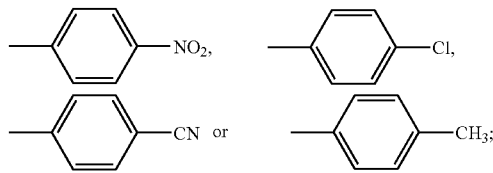

W is benzyl or isobutyl.

2. The compound of claim 1, wherein X is phenyl.

3. The compound of claim 1, wherein W is benzyl.

4. The compound of claim 1, wherein $R_1$ is Methyl.

5. The compound of claim 1, wherein the compound of formula (I) is the following compound of formula (I-1):

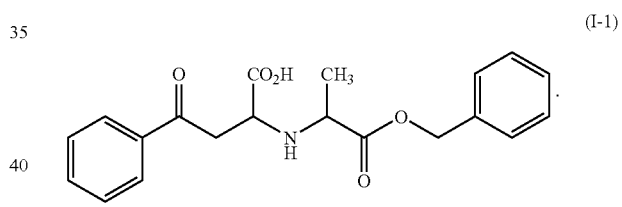

6. A method for preparing a compound of the following formula (I):

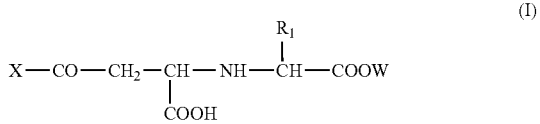

Wherein:

$R_1$ is methyl or 4-aminobutyl, which may be acylated;

X is phenyl,

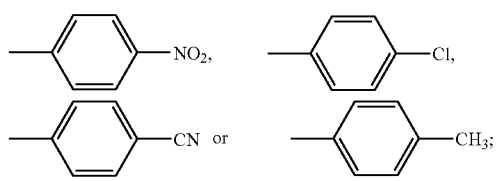

W is benzyl or isobutyl;

Which comprises reacting the following α-amino acid ester

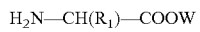

Wherein $R_1$ and W are defined the same as above formula (I) compound, with the following keto-acrylic acid

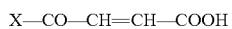

Wherein X is defined the same as above formula (I) compound, to proceed a Michael addition.

7. The method of claim 6, wherein X is phenyl.
8. The method of claim 6, wherein W is benzyl.
9. The method of claim 6, wherein $R_1$ is methyl.

10. The method of claim 6, wherein the compound of formula (I) is the following compound of formula (I-1):

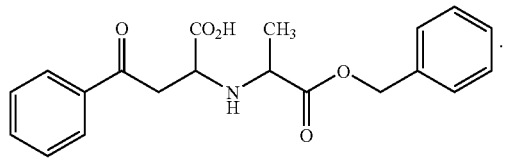

\* \* \* \* \*